(12) United States Patent
Deur-Bert et al.

(10) Patent No.: US 10,640,438 B2
(45) Date of Patent: *May 5, 2020

(54) METHOD FOR PRODUCING TETRAFLUOROPROPENE

(71) Applicant: Arkema France, Colombes (FR)

(72) Inventors: Dominique Deur-Bert, Charly (FR); Dominique Garrait, Charly (FR); Anne Pigamo, Francheville (FR); Laurent Wendlinger, Soucieu en Jarrest (FR)

(73) Assignee: Arkema France, Colombes (FR)

( * ) Notice: Subject to any disclaimer, the term of this patent is extended or adjusted under 35 U.S.C. 154(b) by 0 days.

This patent is subject to a terminal disclaimer.

(21) Appl. No.: 16/099,208

(22) PCT Filed: May 17, 2017

(86) PCT No.: PCT/FR2017/051187
§ 371 (c)(1),
(2) Date: Nov. 6, 2018

(87) PCT Pub. No.: WO2017/198947
PCT Pub. Date: Nov. 23, 2017

(65) Prior Publication Data
US 2019/0210943 A1     Jul. 11, 2019

(30) Foreign Application Priority Data
May 19, 2016   (FR) ...................................... 16 54445

(51) Int. Cl.
*C07C 17/20* (2006.01)
*B01J 8/04* (2006.01)
(Continued)

(52) U.S. Cl.
CPC ........... *C07C 17/206* (2013.01); *B01J 8/0457* (2013.01); *B01J 8/0492* (2013.01); *B01J 19/02* (2013.01);
(Continued)

(58) Field of Classification Search
CPC ....... C07C 7/013; C07C 17/206; C07C 21/18; B01J 8/025; B01J 8/0278; B01J 19/2445; B01J 2219/00038; Y02P 20/584
See application file for complete search history.

(56) References Cited

U.S. PATENT DOCUMENTS

2014/0012051 A1* 1/2014 Pigamo .................... B01J 37/14
570/160

FOREIGN PATENT DOCUMENTS

WO    2007/079431 A2    7/2007
WO    2008/040969 A1    4/2008
(Continued)

OTHER PUBLICATIONS

ISA/EP; International Search Report and Written Opinion for International Application No. PCT/FR2017/051187 dated Sep. 13, 2017.

*Primary Examiner* — Jafar F Parsa
(74) *Attorney, Agent, or Firm* — NK Patent Law

(57) ABSTRACT

The present invention concerns a method for preparing tetrafluoropropene utilising three reactors and comprising the steps of (a) implementing, in the first and second reactors, at least one step of reacting, in the gas phase, a compound B in the presence of hydrofluoric acid and a catalyst, in alternation with a step of regenerating the catalyst by bringing it into contact with a regeneration flow comprising an oxidising agent, (b) implementing, in the third reactor, a preliminary step of producing the compound B, in alternation with a step of regenerating the preliminary catalyst with a regeneration flow comprising an oxidising
(Continued)

agent. The step of regenerating the preliminary catalyst in the third reactor is implemented in the absence of a step of reacting the compound B in the presence of hydrofluoric acid in said first and second reactors. The present invention also concerns a facility configured to implement the present method.

9 Claims, 14 Drawing Sheets

(51) Int. Cl.
*B01J 19/02* (2006.01)
*B01J 38/12* (2006.01)
*C07C 21/18* (2006.01)

(52) U.S. Cl.
CPC ............... *B01J 38/12* (2013.01); *C07C 21/18* (2013.01); *B01J 2208/00371* (2013.01); *B01J 2219/0286* (2013.01); *B01J 2219/0295* (2013.01)

(56) References Cited

FOREIGN PATENT DOCUMENTS

| WO | 2008/054781 A1 | 5/2008 |
|----|----------------|--------|
| WO | 2009/118628 A1 | 10/2009 |
| WO | 2012/098421 A1 | 7/2012 |
| WO | 2012/098422 A1 | 7/2012 |
| WO | 2013/088195 A1 | 6/2013 |
| WO | 2013/182816 A1 | 12/2013 |
| WO | 2016/001515 A1 | 1/2016 |

* cited by examiner

METHOD FOR PRODUCING TETRAFLUOROPROPENE

CROSS-REFERENCE TO RELATED APPLICATIONS

This application is a National Stage application of International Application No. PCT/FR2017/051187, filed on May 17, 2017, which claims the benefit of the French Patent Application No. 1654445, filed on May 19, 2016, the entire contents of which are all hereby incorporated herein by reference.

FIELD OF THE INVENTION

The present invention relates to a process for the manufacture of tetrafluoropropene (HFO-1234) and in particular of 2,3,3,3-tetrafluoropropene (HFO-1234yf), and to a plant suitable for the implementation of this process.

TECHNOLOGICAL BACKGROUND

Greenhouse gases are gaseous components which absorb the infrared radiation emitted by the surface of the earth, thus contributing to the greenhouse effect. The increase in their concentration in the atmosphere is one of the factors causing global warming.

The production of the chlorofluorocarbons (CFCs) and hydrochlorofluorocarbons (HCFCs) used in refrigeration and air conditioning systems has thus been successively regulated by the Montreal protocol and then the Kyoto protocol. There exists a need to develop new molecules which are just as effective and which in particular exhibit the smallest possible global warming potential. This is the case with hydrofluoroolefins and in particular HFO-1234yf, which is a particularly useful compound.

It is known to produce hydrofluoroolefins or hydrofluorocarbons by fluorination of hydrochloroolefins or of hydrochlorocarbons in particular. This fluorination is generally a catalytic fluorination using hydrofluoric acid as fluorinating agent.

The fluorination reaction generally has to be carried out at a high temperature (more than 300° C.) in the gas phase, in the presence of a supported or bulk solid catalyst.

It is known to provide cofeeding with an oxidizing agent, in particular air, or optionally chlorine, in order to preserve the lifetime of the catalyst and to limit the deposition of coke at its surface during the reaction stage.

The document U.S. Pat. No. 8,614,361 describes a process for the manufacture of HFO-1234yf by reacting HCFO-1233xf with HF in the presence of a high oxygen content.

The document U.S. Pat. No. 8,618,338 describes a process for the manufacture of fluoroolefin in two stages, in particular a first stage of reaction in the liquid phase starting from 1,1,2,3-tetrachloropropene (HCO-1230xa), in order to obtain the intermediate HCFO-1233xf, and a second stage of reaction in the gas phase starting from HCFO-1233xf, in order to obtain HFO-1234yf.

The document WO 2013/088195 teaches a process for the manufacture of HFO-1234yf in two stages, a first stage of fluorination in the gas phase of 1,1,1,2,3-pentachloropropane (HCC-240db) and/or of 1,1,2,2,3-pentachloropropane (HCC-240aa), in order to obtain the intermediate HCFO-1233xf, and then a second stage of reaction in the gas phase starting from HCFO-1233xf, in order to obtain HFO-1234yf.

The documents WO 2012/098421 and WO 2012/098422 teach the activation and the regeneration of fluorination catalysts.

The document WO 2013/182816 describes a chemical reaction process for the alternating implementation of a phase of catalytic reaction and of a phase of regeneration of catalyst in a reactor.

The document WO2016/001515 describes a chemical reaction process for the alternating implementation of a phase of catalytic reaction and of a phase of regeneration of catalyst in one or more reactors.

There still exists a need to improve the processes for the manufacture of HFO-1234 compounds, such as HFO-1234yf, and in particular to produce these compounds with a high yield and with a high degree of purity while minimizing the production costs and the capital costs.

SUMMARY OF THE INVENTION

The present invention relates, according to a first aspect, to a process for the manufacture of tetrafluoropropene employing three reactors and comprising the stages of:
carrying out, in the first and the second reactor, at least one stage of reaction in the gas phase of a compound B in the presence of hydrofluoric acid and of a catalyst, in order to form the tetrafluoropropene; alternately with a stage of regeneration of the catalyst by bringing the latter into contact with a regeneration stream comprising an oxidizing agent,
carrying out, in the third reactor, a preliminary stage of manufacture of the compound B, which is preferably a preliminary stage of reaction in the gas phase of a compound A in the presence of hydrofluoric acid and of a preliminary catalyst, said compound A being different from said compound B, alternately with a stage of regeneration of the preliminary catalyst with a regeneration stream comprising an oxidizing agent,
characterized in that:
the stage of regeneration of the preliminary catalyst in the third reactor is carried out in the absence of stage of reaction of the compound B in the presence of hydrofluoric acid in said first and second reactors.
According to one embodiment, the process comprises:
the collecting of a stream of products on conclusion of the preliminary stage of manufacture of the compound B;
the use of said stream of products in order to carry out the stage of reaction of the compound B in the presence of hydrofluoric acid; and
the separation of the stream of products resulting from the stage of reaction of the compound B in the presence of hydrofluoric acid into a first stream comprising hydrochloric acid and tetrafluoropropene and a second stream comprising hydrofluoric acid and the compound B;
optionally, the collecting of said second stream comprising hydrofluoric acid and the compound B, and the recycling of this in the stage of reaction of the compound B in the presence of hydrofluoric acid or of the preliminary stage of manufacture of the compound B.

According to one embodiment, the stage of regeneration of the preliminary catalyst in the third reactor is carried out simultaneously with the stage of regeneration of the catalyst in the first reactor or the second reactor or both; or in the absence of stage of regeneration of the catalyst in the first reactor or the second reactor or both. In this case, the first reactor and/or the second reactor can be in the regeneration phase or in the waiting phase, that is to say a phase during which no stream circulates or only a stream consisting of an inert gas.

According to one embodiment, in the first reactor and the second reactor, the stage of reaction of a compound B in the presence of hydrofluoric acid is carried out alternately with the regeneration stage.

According to one embodiment, the reactors are made of steel and have an interior surface covered with an alloy comprising more than 30% by weight of nickel or with a coating of fluoropolymers type; preferably, the alloy comprising more than 30% by weight of nickel is an Incolloy®, Inconel®, Monel® or Hastelloy®.

According to a preferred embodiment, the tetrafluoropropene is 2,3,3,3-tetrafluoropropene or 1,3,3,3-tetrafluoropropene.

According to a preferred embodiment, the compound A is chosen from tetrachloropropenes, chlorotrifluoropropenes, pentachloropropanes, dichlorotrifluoropropanes, trichlorodifluoropropanes, tetrachlorofluoropropanes, dichlorodifluoropropenes, trichlorofluoropropenes and the mixtures of these; the compound B is chosen from chlorotrifluoropropenes, pentafluoropropanes, dichlorotrifluoropropanes, trichlorodifluoropropanes, tetrachlorofluoropropanes, dichlorodifluoropropenes, trichlorofluoropropenes and the mixtures of these; preferably, the compound A is selected from the group consisting of 2-chloro-3,3,3-trifluoro-1-propene (HFCO-1233xf), 2,3-dichloro-1,1,1-trifluoropropane (HCFC-243db), 1,1,1,2,3-pentachloropropane (HCC-240db), 1,1,2,2,3-pentachloropropane (HCC-240aa), 1,1,1,3,3-pentachloropropane (HCC-240fa), 1,1,2,3-tetrachloro-1-propene (HCO-1230xa), 2,3,3,3-tetrachloro-1-propene (HCO-1230xf), 1,1,3,3-tetrachloro-1-propene (HCO-1230za) and 1,3,3,3-tetrachloro-1-propene (HCO-1230zd); and the compound B is selected from the group consisting of 2-chloro-3,3,3-trifluoro-1-propene (HCFO-1233xf), 1,1,1,2,2-pentafluoropropane (HFC-245cb) and 1-chloro-3,3,3-trifluoro-1-propene (HCFO-1233zd).

According to a preferred embodiment, the regeneration stream is in the same direction or in the reverse direction, preferably in the reverse direction, with respect to the direction of introduction into the first reactor or the second reactor of a reaction stream comprising the compound B and hydrofluoric acid.

According to a preferred embodiment, the direction of the regeneration stream is alternated at each regeneration stage.

The invention also relates to a plant for the manufacture of tetrafluoropropene, comprising three reactors for reaction in the gas phase comprising a catalyst bed, the first reactor and the second reactor for reaction in the gas phase being each configured in order to be fed in turn by:
  a device for feeding with reaction stream comprising a compound B and hydrofluoric acid; and
  a device for feeding with regeneration stream configured in order to feed the reactor with a regeneration stream comprising an oxidizing agent; and
the third reactor for reaction in the gas phase being configured in order to be fed in turn by:
  a device for feeding with reaction stream comprising a compound A and hydrofluoric acid, and optionally an intermediate collecting device connected at the outlet of the first reactor or of the second reactor; said compound A being different from said compound B; and
  a device for feeding with regeneration stream configured in order to feed the reactor with a regeneration stream comprising an oxidizing agent.

According to one embodiment, the plant is configured so that, when the first reactor is fed by the device for feeding with reaction stream, the second reactor is fed by the device for feeding with regeneration stream.

According to one embodiment, the device for feeding with regeneration stream is connected at the top and at the bottom of the reactor.

According to one embodiment, the plant is configured so that the system for feeding with regeneration stream feeds any one of the three reactors at the bottom and at the top alternately.

According to a preferred embodiment, the tetrafluoropropene is 2,3,3,3-tetrafluoropropene or the tetrafluoropropene is 1,3,3,3-tetrafluoropropene.

According to a preferred embodiment, the compound A is chosen from tetrachloropropenes, chlorotrifluoropropenes, pentachloropropanes, dichlorotrifluoropropanes, trichlorodifluoropropanes, tetrachlorofluoropropanes, dichlorodifluoropropenes, trichlorofluoropropenes and the mixtures of these; the compound B is chosen from chlorotrifluoropropenes, pentafluoropropanes, dichlorotrifluoropropanes, trichlorodifluoropropanes, tetrachlorofluoropropanes, dichlorodifluoropropenes, trichlorofluoropropenes and the mixtures of these; preferably, the compound A is selected from the group consisting of 2-chloro-3,3,3-trifluoro-1-propene (HFCO-1233xf), 2,3-dichloro-1,1,1-trifluoropropane (HCFC-243db), 1,1,1,2,3-pentachloropropane (HCC-240db), 1,1,2,2,3-pentachloropropane (HCC-240aa), 1,1,1,3,3-pentachloropropane (HCC-240fa), 1,1,2,3-tetrachloro-1-propene (HCO-1230xa), 2,3,3,3-tetrachloro-1-propene (HCO-1230xf), 1,1,3,3-tetrachloro-1-propene (HCO-1230za) and 1,3,3,3-tetrachloro-1-propene (HCO-1230zd); and the compound B is selected from the group consisting of 2-chloro-3,3,3-trifluoro-1-propene (HCFO-1233xf), 1,1,1,2,2-pentafluoropropane (HFC-245cb) and 1-chloro-3,3,3-trifluoro-1-propene (HCFO-1233zd).

According to a preferred embodiment, the plant comprises:
  a first reactor;
  a second reactor;
  a third reactor;
  a device for collecting stream of products resulting from the third reactor connected at the outlet of the third reactor;
  a separation unit fed by the device for collecting stream of products resulting from the third reactor;
  a first collecting pipe and a second collecting pipe which are connected at the outlet of the separation unit, the first collecting pipe being configured in order to transport a stream comprising hydrochloric acid and tetrafluoropropene and the second collecting pipe being configured in order to transport a stream comprising hydrofluoric acid and the compound B;
  an intermediate collecting device connected at the outlet of the first reactor and/or of the second reactor;
  a first device for feeding the third reactor configured in order to feed the third reactor, this device being itself fed by the device for feeding with preliminary reaction mixture and optionally by the intermediate collecting device;
  a second device for feeding with reaction medium configured in order to alternately feed the second reactor and the first reactor, this device being itself fed by the second collecting pipe and optionally by a device for feeding with hydrofluoric acid;
a device for feeding with regeneration stream configured in order to feed the first reactor and the second reactor;
a device for feeding with regeneration stream configured in order to feed the third reactor;
a device for collecting stream of gas resulting from the regeneration of the first reactor and of the second reactor; and
a device for collecting stream of gas resulting from the regeneration of the third reactor.

According to a preferred embodiment, the plant comprises:
a first reactor;
a second reactor;
a third reactor;
a device for collecting stream of products connected at the outlet of the first reactor and of the second reactor;
a separation unit fed by the device for collecting stream of products;
a first collecting pipe and a second collecting pipe which are connected at the outlet of the separation unit, the first collecting pipe being configured in order to transport a stream comprising hydrochloric acid and tetrafluoropropene and the second collecting pipe being configured in order to transport a stream comprising hydrofluoric acid and the compound B;
an intermediate collecting device connected at the outlet of the third reactor;
a first device for feeding the third reactor configured in order to feed the third reactor, this device being itself fed by the device for feeding with preliminary reaction mixture and optionally by the second collecting pipe;
a second device for feeding with reaction medium configured in order to feed the first reactor or the second reactor, this device being itself fed by the intermediate collecting device and optionally by a device for feeding with hydrofluoric acid;
a device for feeding with regeneration stream configured in order to feed the first reactor and the second reactor;
a device for feeding with regeneration stream configured in order to feed the third reactor;
a device for collecting stream of gas resulting from the regeneration of the first reactor and of the second reactor; and
a device for collecting stream of gas resulting from the regeneration of the third reactor.

According to a preferred embodiment, the reactors of the plant are made of steel and have an interior surface covered with an alloy comprising more than 30% by weight of nickel or with a coating of fluoropolymers type; preferably, the alloy comprising more than 30% by weight of nickel is an Incolloy®, Inconel®, Monel® or Hastelloy®.

The present invention makes it possible to overcome the disadvantages of the state of the art. It more particularly provides a process for the manufacture of HFO-1234 (and in particular of HFO-1234yf) which has a high yield and which provides the desired product in a high degree of purity, while being more economical.

This is accomplished by virtue of the discovery by the present inventors that the regeneration stage can be optimized, without the lifetime of the catalyst being visibly affected over a predetermined period. In addition, some reaction stages can be carried out essentially in the absence of oxidizing agent. An advantage resulting therefrom is that a gaseous stream of HFO-1234 of a higher purity is obtained as it is obtained essentially in the absence of oxygen during the reaction. In addition, the use of reactors, only the interior surface of which is in an alloy as defined in the present invention, renders the process more viable economically while maintaining a high resistance to corrosion.

DETAILED DESCRIPTION OF THE INVENTION

Figure 1A:
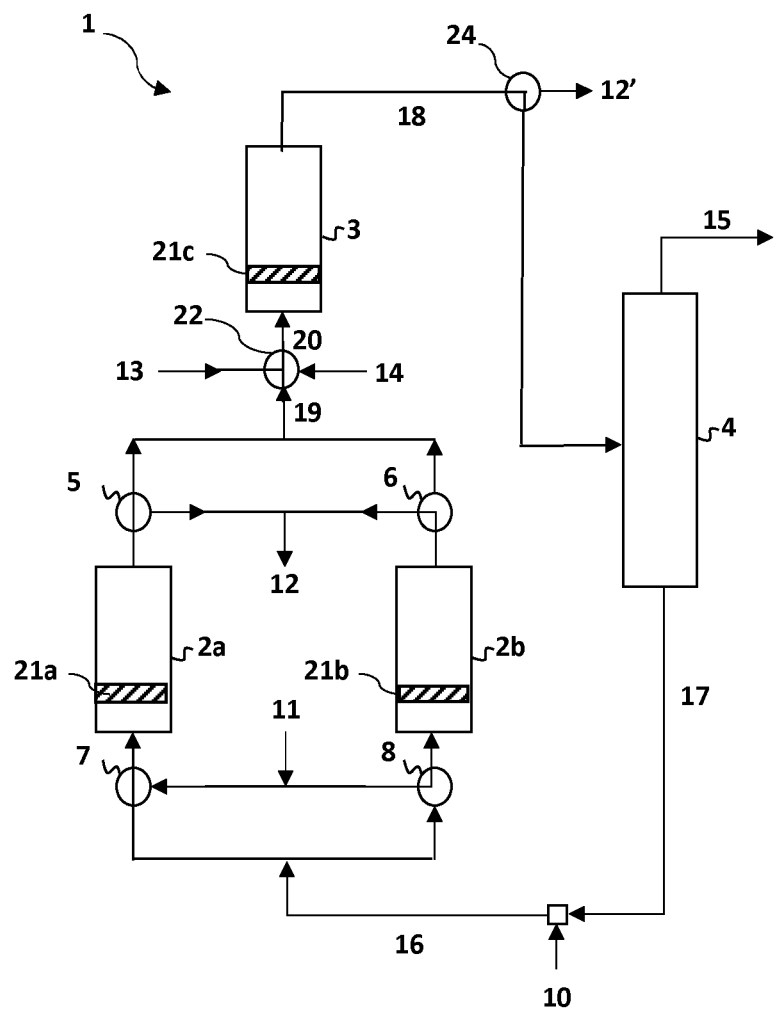
FIGS. 1a, 1b and 1c diagrammatically represent an embodiment of a plant according to the invention with three reactors for catalytic reaction in different operating configurations.

The invention is now described in greater detail and in a nonlimiting manner in the description which follows. Unless otherwise mentioned, the percentages and proportions shown are values by weight. The invention provides for the production of HFO-1234 by catalytic reaction in the gas phase; this catalytic reaction is, according to the invention, alternated with the regeneration of the catalyst. In some embodiments, the invention provides for the production of HFO-1234 in several stages.

According to a first aspect, the present invention provides a process for the manufacture of tetrafluoropropene. Said process for the manufacture of tetrafluoropropene employs three reactors. The process according to the present invention comprises in particular a stage of carrying out, in the first reactor and the second reactor, at least one stage of reaction in the gas phase of a compound B in the presence of hydrofluoric acid and of a catalyst; alternately with a stage of regeneration of the catalyst by bringing the latter into contact with a regeneration stream comprising an oxidizing agent. Said process can also comprise a stage of carrying out, in the third reactor, a preliminary stage of manufacture of the compound B, which is preferably a preliminary stage of reaction in the gas phase of a compound A in the presence of hydrofluoric acid and of a preliminary catalyst, said compound A being different from said compound B, alternately with a stage of regeneration of the preliminary catalyst with a regeneration stream comprising an oxidizing agent. In addition, in the present process, the stage of regeneration of the preliminary catalyst in the third reactor can be carried out in the absence of stage of reaction of the compound B in the presence of hydrofluoric acid in said first and second reactors.

Thus, according to one embodiment, said process for the manufacture of tetrafluoropropene in the three reactors comprises the stages of:
carrying out, in the first and the second reactor, at least one stage of reaction in the gas phase of a compound B in the presence of hydrofluoric acid and of a catalyst, in order to form the tetrafluoropropene; alternately with a stage of regeneration of the catalyst by bringing the latter into contact with a regeneration stream comprising an oxidizing agent, carrying out, in the third reactor, a preliminary stage of manufacture of the compound B, which is preferably a preliminary stage of reaction in the gas phase of a compound A in the presence of hydrofluoric acid and of a preliminary catalyst, said compound A being different from said compound B, alternately with a stage of regeneration of the preliminary catalyst with a regeneration stream comprising an oxidizing agent, characterized in that:

the stage of regeneration of the preliminary catalyst in the third reactor being carried out in the absence of stage of reaction of the compound B in the presence of hydrofluoric acid in said first and second reactors.

According to a preferred embodiment, when the third reactor is in the regeneration phase, that is to say that the stage of regeneration of the preliminary catalyst is carried out in this third reactor, the first reactor and the second reactor are, independently of one another, either in the phase of regeneration of the catalyst or in the waiting phase, during which no flow circulates or a flow consisting of an inert gas, such as nitrogen, argon or helium, circulates in the reactor under consideration or the reactor under consideration is placed under vacuum.

"Compound B" is understood to mean an organic compound comprising one or more carbon atoms. This compound preferably comprises 3 carbon atoms. This compound B is preferably a propane or a propene having one or more substituents chosen from F, Cl, I and Br (preferably from F and Cl). Preferably, the compound B is a propane or propene comprising at least one fluorine atom, in particular comprising two, three, four or five fluorine atoms, more particularly three or five fluorine atoms.

"Compound A" is understood to mean an organic compound comprising one or more carbon atoms, preferably 3 carbon atoms. The compound A is preferably a propane or a propene having one or more substituents chosen from F, Cl, I and Br (preferably from F and Cl). Preferably, the compound A is a propane or propene comprising at least one chlorine atom, two, three, four or five chlorine atoms. Preferably, the compound A has a lower degree of fluorination than that of the compound B.

It is understood that "compound B" or "compound A" is also understood to mean mixtures of compounds.

The compound B can be chosen from chlorotrifluoropropenes, pentafluoropropanes, dichlorotrifluoropropanes, trichlorodifluoropropanes, tetrachlorofluoropropanes, dichlorodifluoropropenes, trichlorofluoropropenes and a mixture of these.

The compound A can be chosen from tetrachloropropenes, chlorotrifluoropropenes, pentachloropropanes, dichlorotrifluoropropanes, trichlorodifluoropropanes, tetrachlorofluoropropanes, dichlorodifluoropropenes, trichlorofluoropropenes and the mixtures of these.

Preferably, the compound B can be chosen from the group consisting of 2-chloro-3,3,3-trifluoro-1-propene (HCFO-1233xf), 2,3-dichloro-1,1,1-trifluoropropane (HCFC-243db), 1,1,1,2,2-pentafluoropropane (HFC-245cb) and 1-chloro-3,3,3-trifluoropropene (HCFO-1233zd).

Preferably, the compound A can be chosen from the group consisting of 2-chloro-3,3,3-trifluoro-1-propene (HCFO-1233xf), 1,1,1,2,3-pentachloropropane (HCC-240db), 1,1,2,2,3-pentachloropropane (HCC-240aa), 2,3-dichloro-1,1,1-trifluoropropane (HCFC-243db), 1,1,2,3-tetrachloro-1-propene (HCO-1230xa), 2,3,3,3-tetrachloro-1-propene (HCO-1230xf), 1,1,1,3,3-pentachloropropane (HCC-240fa), 1,1,3,3-tetrachloropropene (HCO-1230za), 1,3,3,3-tetrachloropropene (HCO-1230zd), 1-chloro-3,3,3-trifluoropropene (HCFO-1233zd), 1,1,1,3-tetrachloropropane (HCC-250fb), 1,1,3-trichloropropene (HCO-1240za) and 3,3,3-trichloropropene (HCO-1240zf). Advantageously, the compound A used in the third reactor can be different from the compound B used in the first or the second reactor.

In particular, the compound B can be selected from the group consisting of 2-chloro-3,3,3-trifluoro-1-propene (HCFO-1233xf) and 1,1,1,2,2-pentafluoropropane (HFC-245cb).

In particular, the compound A can be selected from the group consisting of 2-chloro-3,3,3-trifluoro-1-propene (HFCO-1233xf), 2,3-dichloro-1,1,1-trifluoropropane (HCFC-243db), 1,1,1,2,3-pentachloropropane (HCC-240db), 1,1,2,2,3-pentachloropropane (HCC-240aa), 1,1,1,3,3-pentachloropropane (HCC-240fa), 1,1,2,3-tetrachloro-1-propene (HCO-1230xa), 2,3,3,3-tetrachloro-1-propene (HCO-1230xf), 1,1,3,3-tetrachloro-1-propene (HCO-1230za) and 1,3,3,3-tetrachloro-1-propene (HCO-1230zd).

In one embodiment, the compound B is 2-chloro-3,3,3-trifluoropropene (HCFO-1233xf), in order to produce 2,3,3,3-tetrafluoropropene (HFO-1234yf).

In another embodiment, the compound B is 1-chloro-3,3,3-trifluoropropene (HCFO-1233zd), in order to produce 1,3,3,3-tetrafluoropropene (HFO-1234ze).

In another embodiment, the compound A is 1,1,1,2,3-pentachloropropane (HCC-240db) or 1,1,2,2,3-pentachloropropane (HCC-240aa) or else a mixture of the two, in order to produce 2,3,3,3-tetrafluoropropene (HFO-1234yf). In particular, the compound A is 1,1,1,2,3-pentachloropropane (HCC-240db) or 1,1,2,2,3-pentachloropropane (HCC-240aa) or else a mixture of the two; and the compound B is 2-chloro-3,3,3-trifluoropropene (HCFO-1233xf), in order to produce 2,3,3,3-tetrafluoropropene (HFO-1234yf).

According to yet another embodiment, the compound A is 2,3-dichloro-1,1,1-trifluoropropane (HCFC-243db), in order to produce 2,3,3,3-tetrafluoropropene (HFO-1234yf). In particular, the compound A is 2,3-dichloro-1,1,1-trifluoropropane (HCFC-243db) and the compound B is 2-chloro-3,3,3-trifluoropropene (HCFO-1233xf), in order to produce 2,3,3,3-tetrafluoropropene (HFO-1234yf).

According to yet another embodiment, the compound A is 1,1,2,3-tetrachloropropene (HCO-1230xa) or 2,3,3,3-tetrachloropropene (HCO-1230xf) or a mixture of these two compounds, in order to produce 2,3,3,3-tetrafluoropropene (HFO-1234yf). In particular, the compound A is 1,1,2,3-tetrachloropropene (HCO-1230xa) or 2,3,3,3-tetrachloropropene (HCO-1230xf) or a mixture of these two compounds; and the compound B is 2-chloro-3,3,3-trifluoropropene (HCFO-1233xf), in order to produce 2,3,3,3-tetrafluoropropene (HFO-1234yf).

According to yet another embodiment, the compound A is 1,1,2,3-tetrachloropropene (HCO-1230xa) or 2,3,3,3-tetrachloropropene (HCO-1230xf) or 1,1,1,2,3-pentachloropropane (HCC-240db) or a mixture of two of these or a mixture of the three; and the compound B is 2-chloro-3,3,3-trifluoropropene (HCFO-1233xf), in order to produce 2,3,3,3-tetrafluoropropene (HFO-1234yf).

According to another embodiment, the compound A is 1,1,3,3-tetrachloropropene (HCO-1230za) or 1,3,3,3-tetrachloro-1-propene (HCO-1230zd) or a mixture of the two;

and the compound B is 1-chloro-3,3,3-trifluoropropene (HCFO-1233zd), in order to produce 1,3,3,3-tetrafluoropropene (HFO-1234ze).

According to another embodiment, the compound A is 1,1,1,3,3-pentachloropropane (HCC-240fa) and the compound B is 1-chloro-3,3,3-trifluoropropene (HCFO-1233zd), in order to produce 1,3,3,3-tetrafluoropropene (HFO-1234ze).

According to one embodiment, the compound B is 1,1,1,2,2-pentafluoropropane (HFC-245cb), in order to produce 2,3,3,3-tetrafluoropropene (HFO-1234yf). Preferably, the compound A is 2-chloro-3,3,3-trifluoropropene (HCFO-1233xf) and the compound B is 1,1,1,2,2-pentafluoropropane (HFC-245cb), in order to produce 2,3,3,3-tetrafluoropropene (HFO-1234yf).

The conversion of the compound B to give HFO-1234 can be a direct conversion or an indirect conversion (that is to say, involving an intermediate product).

The reaction of the compound B to give HFO-1234 is carried out in two reactors for reaction in the gas phase comprising a catalyst bed. The reaction of the compound A to give compound B is carried out in a reactor in the gas phase comprising a preliminary catalyst bed. Said catalyst used in the first and the second reactor can be identical to the preliminary catalyst used in the third reactor.

The catalyst or the preliminary catalyst used in the present process can, for example, be based on a metal comprising a transition metal oxide or a derivative or a halide or an oxyhalide of such a metal. Mention may be made, for example, of $FeCl_3$, chromium oxyfluoride, chromium oxides (optionally subjected to fluorination treatments), chromium fluorides and their mixtures. Other possible catalysts are catalysts supported on carbon, antimony-based catalysts or aluminum-based catalysts (for example $AlF_3$ and $Al_2O_3$, aluminum oxyfluoride and aluminum fluoride).

Use may be made in general of a chromium oxyfluoride, an aluminum fluoride or oxyfluoride, or a supported or nonsupported catalyst containing a metal such as Cr, Ni, Fe, Zn, Ti, V, Zr, Mo, Ge, Sn, Pb, Mg or Sb.

Reference may be made, in this regard, to the document WO 2007/079431 (on p. 7, I. 1-5 and 28-32), to the document EP 939 071 (section [0022]), to the document WO 2008/054781 (on p. 9, I. 22-p. 10, I. 34) and to the document WO 2008/040969 (claim 1), to which documents reference is expressly made.

The catalyst is more particularly preferably chromium-based and it is more particularly a mixed catalyst comprising chromium.

According to one embodiment, use is made, for any one of the reaction stages, of a mixed catalyst comprising chromium and nickel. The Cr/Ni molar ratio (on the basis of the metal element) is generally from 0.5 to 5, for example from 0.7 to 2, for example approximately 1. The catalyst can contain from 0.5% to 20% by weight of nickel.

The metal can be present in metallic form or in the form of a derivative, for example an oxide, halide or oxyhalide. These derivatives are preferably obtained by activation of the catalytic metal.

The support is preferably formed with aluminum, for example alumina, activated alumina or aluminum derivatives, such as aluminum halides and aluminum oxyhalides, for example described in the document U.S. Pat. No. 4,902,838, or obtained by the activation process described above.

The catalyst can comprise chromium and nickel in an activated or nonactivated form, on a support which has or has not been subjected to an activation.

Reference may be made to the document WO 2009/118628 (in particular on p. 4, I. 30-p. 7, I. 16), to which reference is expressly made here.

Another preferred embodiment is based on a mixed catalyst or mixed preliminary catalyst containing chromium and at least one cocatalyst chosen from Co, Mn, Mg and Zn salts, preferably Zn salts. Said cocatalyst is preferably present in a content of 1% to 10% by weight, based on the weight of the catalyst.

Before its use, the catalyst or the preliminary catalyst is preferably subjected to an activation with air, oxygen or chlorine and/or with HF. For example, the catalyst is preferably subjected to an activation with air or oxygen and HF at a temperature of 100 to 500° C., preferably of 250 to 500° C. and more particularly of 300 to 400° C. The duration of activation is preferably from 1 to 200 h and more particularly from 1 to 50 h. This activation can be followed by a final fluorination activation stage in the presence of an oxidizing agent, HF and organic compounds. The HF/organic compounds molar ratio is preferably from 2 to 40 and the oxidizing agent/organic compounds molar ratio is preferably from 0.04 to 25. The temperature of the final activation is preferably from 300 to 400° C. and its duration is preferably from 6 to 100 h.

The reaction in the gas phase in the presence of hydrofluoric acid with the compound B or the compound A can be carried out:
  with an HF/compound B or compound A molar ratio of 3:1 to 150:1, preferably of 4:1 to 125:1 and more particularly preferably of 5:1 to 100:1;
  with a contact time of 3 to 100 s, preferably 4 to 75 s and more particularly 5 to 50 s (volume of catalyst divided by the total entering stream, adjusted to the operating temperature and pressure);
  at a pressure ranging from atmospheric pressure to 20 bar, preferably from 2 to 18 bar and more particularly from 3 to 15 bar;
  at a temperature (temperature of the catalyst bed) of 200 to 450° C., preferably of 250 to 400° C. and more particularly of 280 to 380° C.

The duration of the reaction stage is typically from 10 to 8000 hours, preferably from 50 to 5000 hours and more particularly preferably from 70 to 1000 hours.

An oxidizing agent, preferably oxygen, can optionally be added during the reaction. The oxygen/organic compounds molar ratio can be from 0.005 to 2, preferably from 0.01 to 1.5. Oxygen can be introduced in the pure form or in the form of air or of an oxygen/nitrogen mixture. Oxygen can also be replaced with chlorine.

Alternatively, the stage of reaction of the compound B or of the compound A in the presence of hydrofluoric acid is essentially carried out in the absence of oxygen and preferably essentially in the absence of any oxidizing agent.

According to a specific embodiment, said process also comprises:
  the collecting of a stream of products on conclusion of the preliminary stage of manufacture of the compound B;
  the use of said stream of products in order to carry out the stage of reaction of the compound B in the presence of hydrofluoric acid; and
  the separation of the stream of products resulting from the stage of reaction of the compound B in the presence of hydrofluoric acid into a first stream comprising hydrochloric acid and tetrafluoropropene and a second stream comprising hydrofluoric acid and the compound B;
  optionally, the collecting of said second stream comprising hydrofluoric acid and the compound B, and the recycling of this in the stage of reaction of the compound B in the presence of hydrofluoric acid or of the preliminary stage of manufacture of the compound B.

According to another specific embodiment, said process also comprises:

the collecting of a stream of products on conclusion of the stage of reaction of the compound B in the presence of hydrofluoric acid;

the use of said stream of products in order to carry out the stage of reaction of the compound A in the presence of hydrofluoric acid in order to form a stream of products in the third reactor;

the separation of the stream of products thus obtained in the third reactor into a first stream comprising hydrochloric acid and tetrafluoropropene and a second stream comprising hydrofluoric acid and the compound B; and optionally, the collecting of said second stream comprising hydrofluoric acid and the compound B, and the recycling of this in the stage of reaction of the compound B in the presence of hydrofluoric acid in the first reactor or the second reactor.

The separation of the streams of products resulting respectively from the stage of reaction of the compound A with HF or from the stage of reaction of the compound B with HF can be carried out by a separation unit which can be a distillation column or any other device capable of separating, on the one hand, hydrochloric acid and tetrafluoropropene and, on the other hand, hydrofluoric acid and the compound B.

In each reactor used for carrying out the reaction of the compound B or of the compound A with HF, said reaction can be alternated with phases of regeneration of the catalyst. It is possible, for example, to pass from the reaction phase to the regeneration phase when the conversion of the compound B falls below a predetermined threshold, for example of 50%. If need be, beforehand, a transition period consisting in decompressing the reaction gas phase is provided. It can be followed by a phase of flushing using an inert gas or else of placing under vacuum with the aim of completely removing the reactants present.

According to a preferred embodiment, the regeneration of the catalyst or of the preliminary catalyst of the present process can comprise the treatment of said catalyst with a gaseous stream containing an oxidant.

According to one embodiment, the oxidant used in the regeneration stage is oxygen or air or an oxygen/nitrogen mixture or chlorine or a chlorine/nitrogen mixture. When the regeneration stage is carried out with air or an oxygen/nitrogen mixture, the proportion of oxygen can be from 5 mol % to approximately 100 mol %, with respect to the mixture of oxygen plus nitrogen.

According to another embodiment, the regeneration stage can be carried out with oxygen or air or an oxygen/nitrogen mixture or chlorine and HF. Advantageously, the regeneration stream contains at least 1 mol % of oxygen, with respect to the total regeneration stream. The proportion of oxygen can be from approximately 2 mol % to approximately 98 mol %, with respect to the mixture of oxygen plus HF, and from approximately 20 mol % to approximately 100 mol %, with respect to the mixture of oxygen plus nitrogen.

The temperature during the regeneration stage can range from 250 to 500° C., preferably from 300 to 450° C., more preferably from 350 to 400° C.

The regeneration stage can be carried out with a contact time of 1 to 200 s, preferably of 1 to 150 s, more preferably of 5 to 100 s; and for a time of 1 to approximately 1500 hours, preferably of 2 to 1000 hours, more preferably of 4 to 500 hours, particularly preferably of 10 to 200 hours, in particular of 15 to 150 hours.

The regeneration stage can be carried out at a pressure ranging from atmospheric pressure up to 20 bar.

According to a preferred embodiment, the temperature during the regeneration stage can be from approximately 250 to 500° C., with a contact time of approximately 1 to 200 s, for a time of 10 to 200 hours and at a pressure ranging from atmospheric pressure to 20 bar.

The regeneration stage makes it possible to recover the initial activity of the catalyst. Several cycles can thus be linked together without to a significant extent detrimentally affecting the activity of the catalyst, which makes it possible to increase its lifetime.

On conclusion of the regeneration stage, the reactor can be placed under vacuum, so as to remove the inert gases and the oxygen introduced, prior to the reintroduction of the organic materials in the presence of hydrofluoric acid.

Preferably, the stage of regeneration of the preliminary catalyst in the third reactor is carried out simultaneously with the stage of regeneration of the catalyst in the first reactor or the second reactor or both; or in the absence of stage of regeneration of the catalyst.

Preferably, in the first and the second reactor, the reaction stage as described above is carried out alternately with the regeneration stage as described above.

According to a specific embodiment, the reaction and regeneration streams can be in the same direction or the reverse direction; preferably, the reaction and regeneration streams are reversed. In particular, the direction of the regeneration stream is alternated at each regeneration stage. Thus, during a first regeneration phase, the reaction and regeneration streams can be in the same direction and then, in a second regeneration phase, the reaction and regeneration streams can be reversed.

According to a specific embodiment, the three reactors used in the present process can be made of steel and have an interior surface covered with an alloy comprising more than 30% by weight of nickel or with a coating of fluoropolymers type; preferably, the alloy comprising more than 30% by weight of nickel can be an Incolloy®, Inconel®, Monel® or Hastelloy®.

According to a second aspect of the present invention, a plant 1 is provided. The plant 1 for the manufacture of tetrafluoropropene comprises three reactors 2a, 2b and 3 for reaction in the gas phase and comprises a catalyst bed 21a, 21b or 21c.

In addition, the first reactor 2a and the second reactor 2b for reaction in the gas phase are each configured in order to be fed in turn by:

a device for feeding with reaction stream 16 comprising a compound B and hydrofluoric acid; and a device for feeding with regeneration stream 11 configured in order to feed the reactor with a regeneration stream comprising an oxidizing agent.

Furthermore, the third reactor 3 for reaction in the gas phase can be configured in order to be fed in turn by:

a device for feeding with reaction stream 13 comprising a compound A and hydrofluoric acid, and optionally an intermediate collecting device 19 connected at the outlet of the first reactor 2a or of the second reactor 2b; said compound A being different from said compound B; and a device for feeding with regeneration stream 14 configured in order to feed the reactor with a regeneration stream comprising an oxidizing agent.

As described above in connection with the process, the reaction stream 16 or 13 can be essentially devoid of oxygen and preferably of any oxidizing agent. On the other hand, the regeneration stream 11 or 14 can contain at least 1 mol % of oxygen, with respect to the total regeneration stream.

The plant can be configured so that, when the first reactor 2a is fed by the device for feeding with reaction stream 16, the second reactor 2b is fed by the device for feeding with regeneration stream 11. Both a device for collecting stream of products resulting from the reaction and a device for collecting stream of gas resulting from the regeneration are connected at the outlet of the reactors 2a and 2b. Device for collecting or device for feeding is understood to mean a single pipe or an assembly of several pipes.

A device of inlet valves 7, 8 and a device of outlet valves 5, 6 are provided in order to make it possible to switch between the devices for feeding with reaction stream 16 or with regeneration stream 11 and the respective devices for collecting 12 and 19 of the first reactor 2a and of the second reactor 2b.

Preferably, the device for feeding with regeneration stream 11 or 14 is connected at the top and at the bottom of the reactor 2a, 2b or 3. This can, for example, be carried out by a device for regulating the regeneration stream forming an integral part of the device for feeding with regeneration stream 11, 14. Said device for regulating the regeneration stream can comprise a plurality of pipes and at least two regulating valves 25, 25' or 24, 24', as illustrated, for example, in FIG. 3a.

Preferably, the plant 1 is configured so that each of the devices for feeding with regeneration stream 11 or 14 respectively feeds the first reactor 2a and the second reactor 2b or the third reactor 3 at the bottom and at the top alternately. The configuration of the valves 25, 25' or 24, 24' of the device for regulating the regeneration stream makes it possible to easily regulate the regeneration streams 11 or 14 in order to alternate a regeneration of a reactor at the top and a regeneration of a reactor at the bottom.

According to another embodiment, the first reactor 2a, the second reactor 2b and/or the third reactor 3 can be regenerated in series, that is to say that the gas stream resulting from the regeneration of one of the reactors 2a or 2b is conveyed to the other reactor 2a or 2b or the third reactor 3 and is used for the regeneration of the catalyst present in the latter.

The plant 1 is suitable for the manufacture of tetrafluoropropene; advantageously, the tetrafluoropropene is 2,3,3,3-tetrafluoropropene or the tetrafluoropropene is 1,3,3,3-tetrafluoropropene. The compounds A and B are as described above in connection with the process for the manufacture of tetrafluoropropene.

According to a preferred embodiment, the plant 1 comprises:
 a first reactor 2a;
 a second reactor 2b;
 a third reactor 3;
 a device for collecting stream of products resulting from the third reactor 18 connected at the outlet of the third reactor 3;
 a separation unit 4 fed by the device for collecting stream of products resulting from the third reactor 18;
 a first collecting pipe 15 and a second collecting pipe 17 which are connected at the outlet of the separation unit 4, the first collecting pipe 15 being configured in order to transport a stream comprising hydrochloric acid and tetrafluoropropene and the second collecting pipe 17 being configured in order to transport a stream comprising hydrofluoric acid and the compound B;
 an intermediate collecting device 19 connected at the outlet of the first reactor 2a or of the second reactor 2b;
 a first device for feeding the third reactor 20 configured in order to feed the third reactor 3, this device being itself fed by the device for feeding with preliminary reaction mixture 13 and optionally by the intermediate collecting device 19;
 a second device for feeding with reaction medium 16 configured in order to alternately feed the second reactor 2b and the first reactor 2a, this device being itself fed by the second collecting pipe 17 and optionally by a device for feeding with hydrofluoric acid 10;
 a device for feeding with regeneration stream 11 configured in order to feed the first reactor 2a and/or the second reactor 2b;
 a device for feeding with regeneration stream 14 configured in order to feed the third reactor 3;
 a first device for collecting stream of gas resulting from the regeneration of the first reactor and/or of the second reactor 12; and
 a second device for collecting stream of gas resulting from the regeneration of the third reactor 12'.

According to an alternative embodiment, when the third reactor 3 is in the regeneration phase, the device for feeding the third reactor 20 is configured in order to feed the third reactor 3 with a regeneration stream comprising an oxidizing agent resulting from the device for feeding with regeneration stream 14.

Alternatively, the plant can comprise:
 a first reactor 2a;
 a second reactor 2b;
 a third reactor 3;
 a device for collecting stream of products 19 connected at the outlet of the first reactor 2a and of the second reactor 2b;
 a separation unit 4 fed by the device for collecting stream of products 19 resulting from the first reactor 2a or from the second reactor 2b;
 a first collecting pipe 15 and a second collecting pipe 17 which are connected at the outlet of the separation unit 4, the first collecting pipe 15 being configured in order to transport a stream comprising hydrochloric acid and tetrafluoropropene and the second collecting pipe 17 being configured in order to transport a stream comprising hydrofluoric acid and the compound B;
 an intermediate collecting device 18 connected at the outlet of the third reactor 3;
 a first device for feeding the third reactor 20 configured in order to feed the third reactor 3, this device being itself fed by the device for feeding with preliminary reaction mixture 13 and optionally by the second collecting pipe 17;
 a second device for feeding with reaction medium 16 configured in order to feed the first reactor 2a or the second reactor 2b, this device being itself fed by the intermediate collecting device 18 and optionally by a device for feeding with hydrofluoric acid 10;
 a device for feeding with regeneration stream 11 configured in order to feed the first reactor 2a and/or the second reactor 2b;
 a device for feeding with regeneration stream 14 configured in order to feed the third reactor 3;
 a first device for collecting stream of gas resulting from the regeneration of the first reactor and/or of the second reactor 12; and a device for collecting stream of gas resulting from the regeneration of the third reactor 12'.

According to an alternative embodiment, when the third reactor 3 is in the regeneration phase, the device for feeding the third reactor 20 is configured in order to feed the third reactor 3 with a regeneration stream comprising an oxidizing agent resulting from the device for feeding with regeneration stream 14.

According to an alternative embodiment, the second collecting pipe 17 can feed the device for feeding with reaction medium 16 configured in order to feed the first reactor 2a or the second reactor 2b instead of feeding the device for feeding the third reader 20 configured in order to feed the third reactor 3.

According to an alternative embodiment, the device for feeding with regeneration stream configured in order to feed the first reactor 2a and the second reactor 2b is common to the device for feeding with regeneration stream configured in order to feed the third reactor 3, that is to say that a single device for feeding with regeneration stream is used to feed the three reactors. The device for feeding with regeneration stream is then configured for this purpose.

Advantageously, the reactors used for the manufacture of tetrafluoropropene are made of steel and have an interior surface covered with an alloy comprising more than 30% by weight of nickel or with a coating of fluoropolymers type; preferably, the alloy comprising more than 30% by weight of nickel is an Incolloy®, Inconel®, Monel® or Hastelloy®.

The plant will be described below in a detailed away in connection with FIGS. 1a to 4c, without being limited thereto.

FIG. 1a illustrates a plant according to an embodiment of the present invention in which a stage of reaction of a compound B is carried out in the first reactor 2a. The reactor 2b is in the regeneration phase. A stage of reaction of a compound A is carried out in the third reactor 3. Each of the reactors 2a, 2b and 3 respectively comprises a catalyst bed 21a, 21b or a preliminary catalyst bed 21c. The first reactor 2a is fed with reaction mixture, i.e. with compound B and with hydrofluoric acid, at the bottom via the feeding device 16, the latter being fed by a device for feeding with hydrofluoric acid 10 and by the second collecting pipe 17 resulting from the separation unit 4. The valve 7 is positioned so as to make it possible to convey the reaction mixture to the first reactor 2a. The second reactor 2b is connected at the bottom to a device for feeding with regeneration stream 11 via a valve 8. The valves 7 and 8 connected to the first reactor 2a and to the second reactor 2b make it possible to change the reactors from a configuration in which a catalytic reaction is carried out to a configuration in which a regeneration stage is carried out. The stream of products resulting from the first reactor 2a is conveyed to the intermediate collecting device 19 via a valve 5 configured for this purpose. The regeneration stream exits from the second reactor 2b in order to be conveyed to the device for collecting stream of gas resulting from the regeneration 12; this being regulated via the valve 6. The valve 22 makes it possible to regulate the streams entering the device for feeding the third reader 20. Thus, said device for feeding the third reader 20 can be fed with the streams originating from the intermediate collecting device 19 and the device for feeding with preliminary reaction mixture 13, or said device for feeding the third reader 20 can be fed by a device for feeding with regeneration stream 14. The stream entering the third reactor 3 is brought into contact with the catalytic bed 21c. The stream of products resulting from the third reactor 3 is subsequently conveyed to the separation unit 4 by the device for collecting stream of products from the third reactor 18. The valve 24 makes it possible to direct the stream of products to the separation unit 4 or to a device for collecting stream of gas resulting from the regeneration of the third reactor 12'. The separation unit 4 comprises a first pipe 15 and a second pipe 17, the first collecting pipe 15 being configured in order to transport a stream comprising hydrochloric acid and tetrafluoropropene and the second collecting pipe 17 being configured in order to transport a stream comprising hydrofluoric acid and the compound B. As represented in FIG. 1a, the regeneration stream in the second reactor 2b and the stream of the reaction mixture in the first reactor 2a are in the same direction.

Figure 1B:
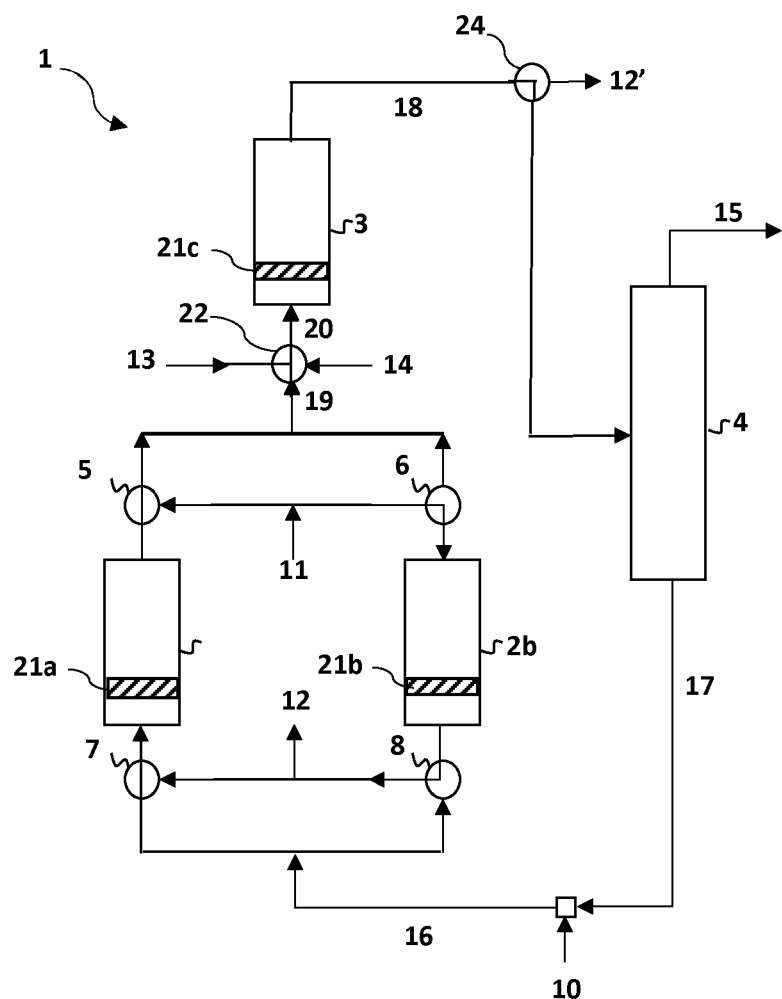

FIG. 1b illustrates an embodiment identical to that presented in FIG. 1a, with the exception of the direction of the regeneration stream and of the reaction stream, i.e. of the reaction mixture, in the first reactor 2a and the second reactor 2b. Thus, in FIG. 1b, the regeneration stream in the second reactor 2b and the reaction stream in the first reactor 2a are reversed. In this case, the device for feeding with regeneration stream 11 feeds the second reactor 2b by the top via the valve 6, whereas the device for feeding with reaction mixture 16 still feeds the first reactor by the bottom of the latter. The regeneration stream exits from the second reactor 2b in order to be conveyed to the device for collecting stream of gas resulting from the regeneration 12 via the valve 8. The third reactor 3 is configured as described in FIG. 1a.

Figure 1C:
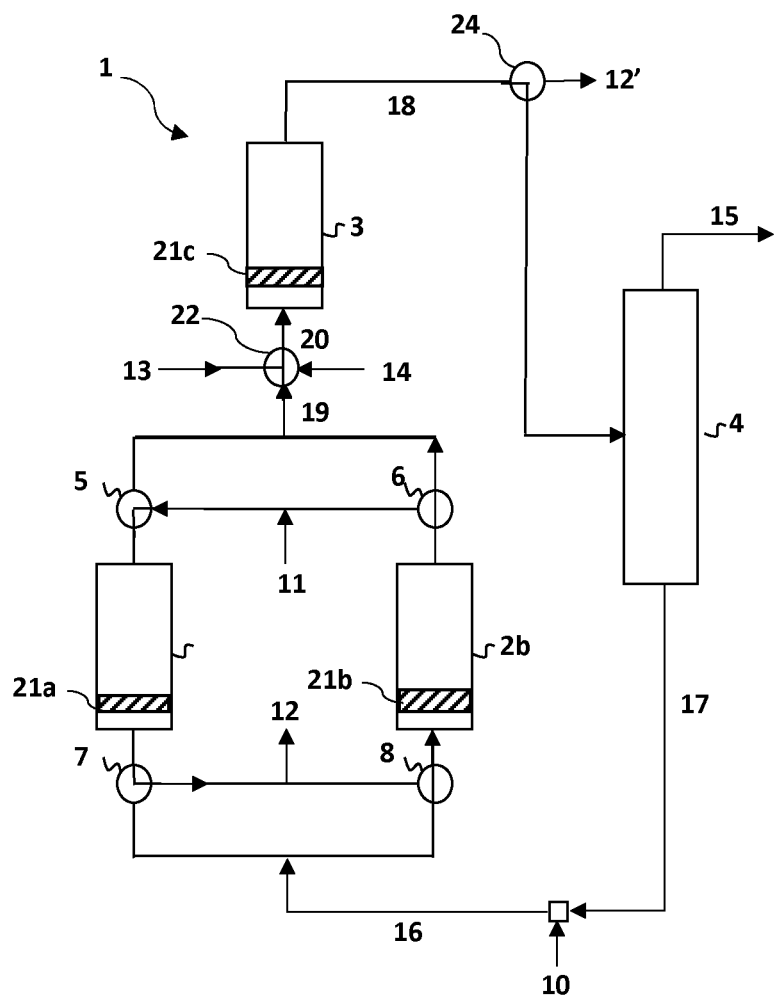

FIG. 1c illustrates an embodiment in which the first reactor 2a is in the regeneration phase, whereas the second reactor 2b is in the reaction phase. The second reactor 2b is fed by the device for feeding with reaction mixture 16 via the valve 8 configured for this purpose. The stream of products resulting from the second reactor 2b feeds the intermediate collecting device 19. Conversely, the first reactor 2a is fed by the device for feeding with regeneration stream 11 by the top of the reactor. The gases present in the first reactor exit, in this case, at the bottom of the reactor to the device for collecting stream of gas resulting from the regeneration 12. The valves 5 and 7 are thus configured in order to make it possible for the regeneration stream to pass inside the first reactor 2a. The third reactor 3 is configured as described in FIG. 1a.

Figure 2A:
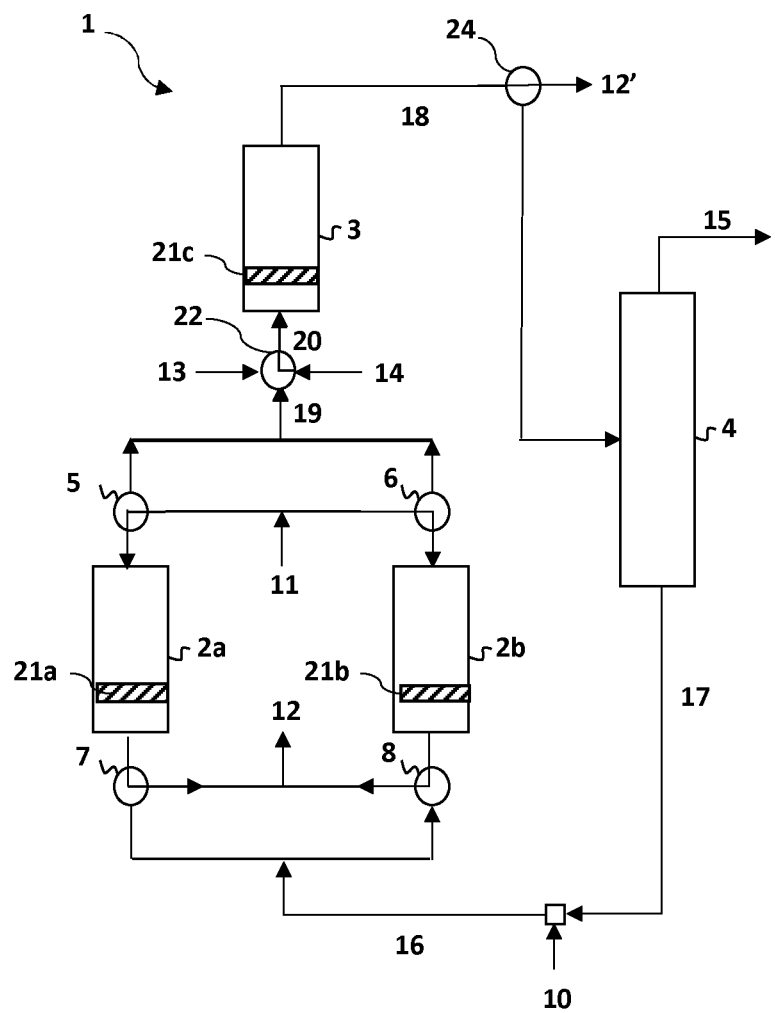
FIGS. 2a, 2b, 2c, 2d and 2e diagrammatically represent an embodiment of a plant according to the invention with three reactors, the third of which is in regeneration mode, in three different configurations.

FIGS. 2a, 2b, 2c, 2d and 2e illustrate embodiments in which the third reactor 3 is in the regeneration phase. As explained above, in this case, the first reactor 2a and the second reactor 2b are not in the reaction phase. The first reactor 2a and the second reactor 2b are, independently of one another, either in the regeneration phase or in the waiting phase, during which no stream circulates inside these. More particularly, FIG. 2a illustrates a plant according to an embodiment in which a stage of regeneration of the catalyst is carried out in the first reactor 2a and in the second reactor 2b. A stage of regeneration of the preliminary catalyst is carried out in the third reactor 3. Each of the reactors 2a, 2b and 3 respectively comprises a catalyst bed 21a, 21b or a preliminary catalyst bed 21c. The first reactor 2a and the second reactor 2b are fed at the top with a regeneration stream dispensed by the device for feeding with regeneration stream 11. The valves 5 and 6 are positioned so as to make it possible to convey the regeneration stream to the first reactor 2a and the second reactor 2b. The stream of gas resulting from the regeneration in the first reactor 2a and the second reactor 2b are discharged to the device for collecting stream of gas resulting from the regeneration 12. The valves 7 and 8 are configured so as to make it possible to convey the stream of gas resulting from the regeneration of the reactors 2a and 2b to the device for collecting stream of gas resulting from the regeneration 12. The third reactor 3 is fed at the bottom by a feeding device 20 comprising a regeneration stream resulting from the device for feeding with regeneration stream 14 via the valve 22 configured for this purpose. The regeneration stream passes through the catalytic bed 21c of the third reactor 3. The stream of gas resulting from the regeneration exits at the top of the third reactor 3 to the device for collecting products resulting from the third reactor 18. This regeneration gas stream is conveyed to the device for collecting the streams of gas resulting from the regeneration 12'. The valve 24 is thus configured in order to connect the device for collecting products resulting from the third reactor 18 to the device for collecting the streams of gas resulting from the regeneration 12'. The device for collecting the streams of gas resulting from the regeneration 12' can be identical to the device for collecting the streams of gas resulting from the regeneration 12. Alternatively, it is possible to have a single device for collecting the streams of gas resulting from the regeneration 12. In this case, the device for collecting products resulting from the third reactor 18 is connected to the device for collecting the streams of gas resulting from the regeneration 12, this device also being fed by the streams of gas resulting from the regeneration of the first reactor 2a and of the second reactor 2b.

Figure 2B:
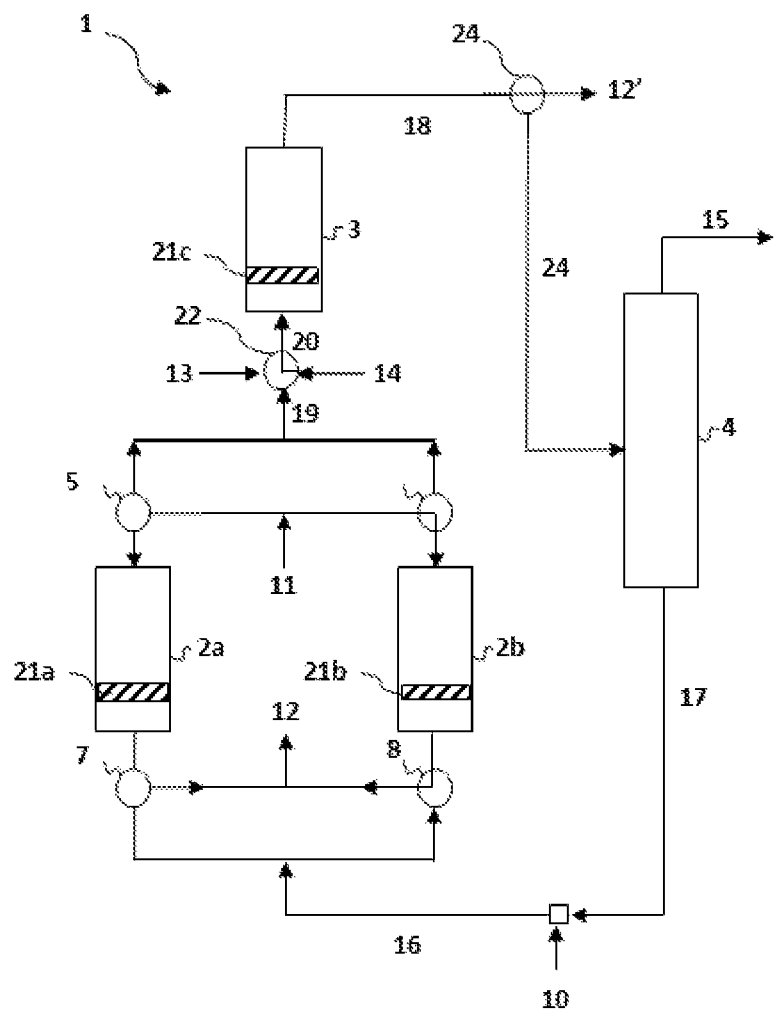

FIG. 2b illustrates an embodiment of the present invention in which the second reactor 2b and the third reactor 3 are in the regeneration phase, whereas the first reactor 2a is in the waiting phase. Thus, the second reactor 2b is fed at the top by the device for feeding with regeneration stream 11. The regeneration stream passes through the catalytic bed 21b in order to exit at the bottom of the second reactor 2b and to be conveyed to the device for collecting the stream of gas resulting from the regeneration 12. The third reactor 3 is fed at the bottom by a feeding device 20 comprising a regeneration stream resulting from the device for feeding with regeneration stream 14 via the valve 22 configured for this purpose. The regeneration stream passes through the catalytic bed 21c of the third reactor 3. The stream of gas resulting from the regeneration exits at the top of the third reactor 3 to the device for collecting products resulting from the third reactor 18. This regeneration gas stream is conveyed to the device for collecting the streams of gas resulting from the regeneration 12'. The valve 24 is thus configured in order to connect the device for collecting products resulting from the third reactor 18 to the device for collecting the streams of gas resulting from the regeneration 12'. No stream circulates in the first reactor 2a. The valves 5 and 7 are configured for this purpose.

Figure 2C:
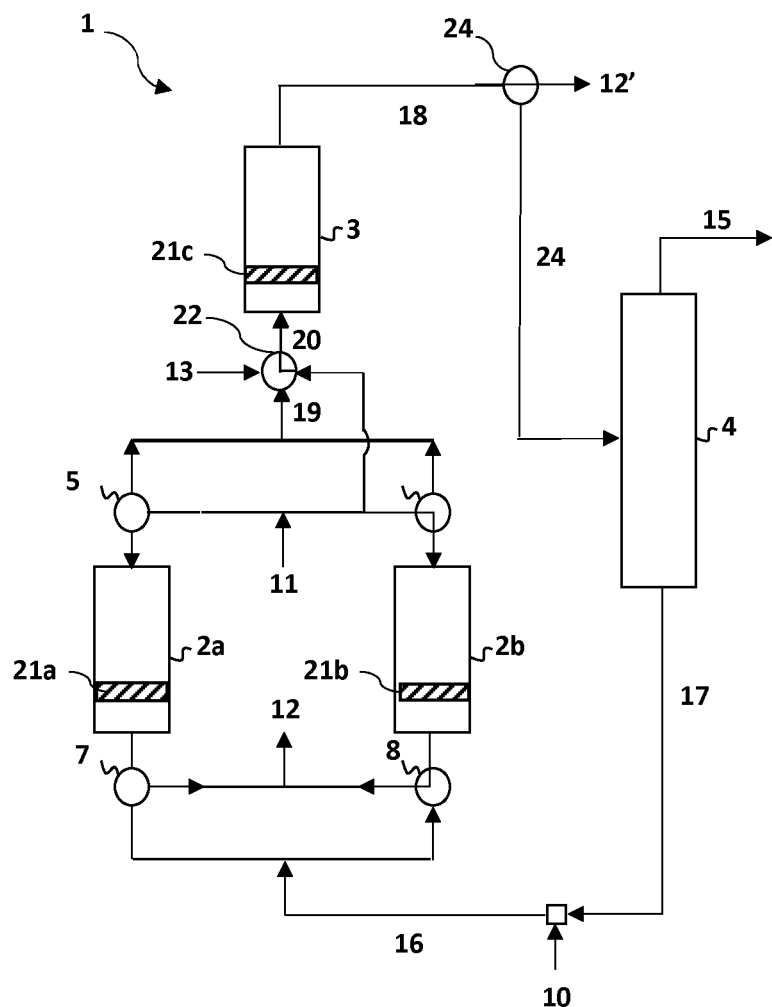

FIG. 2c illustrates a specific embodiment of the present invention in which the second reactor 2b and the third reactor 3 are in the regeneration phase, whereas the first reactor 2a is in the waiting phase, the second reactor 2a and the third reactor 3 being fed with regeneration stream by the same device for feeding with regeneration stream 11. The regeneration stream 11 is conveyed to the third reactor 3 via the feeding device 20 and the valve 22 configured for this purpose.

Figure 2D:
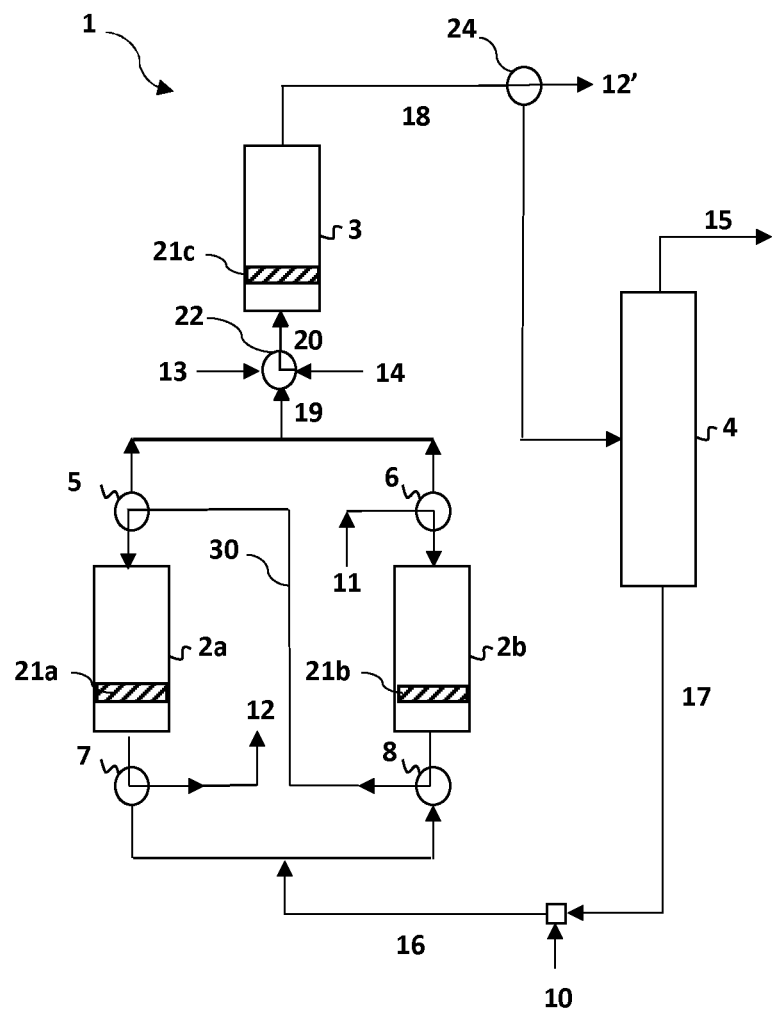

FIG. 2d illustrates a specific embodiment of the present invention in which the first reactor 2a, the second reactor 2b and the third reactor 3 are in the regeneration phase. The first reactor 2a and the second reactor 2b are regenerated in series. Thus, the regeneration stream 11 feeds the second reactor 2b by the top of the reactor via the valve 6. The regeneration stream is discharged at the bottom of the reactor 2b in order to be conveyed via the valve 8, the pipe 30 and the valve 5 to the top of the first reactor 2a. The regeneration stream is injected into the first reactor 2a in order to exit at the reactor bottom. The stream of gas resulting from the regeneration is collected in the device for collecting the streams of gas resulting from the regeneration 12.

Figure 2E:
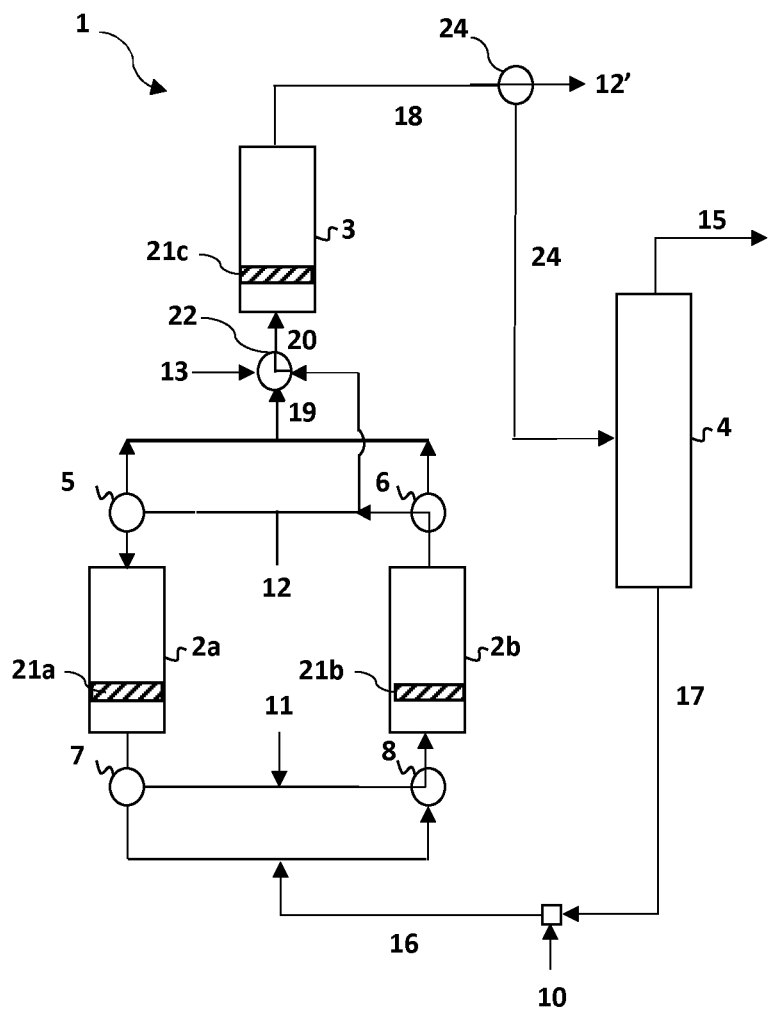

FIG. 2e illustrates a specific embodiment of the present invention in which the second reactor 2b and the third reactor 3 are in the regeneration phase, whereas the first reactor 2a is in the waiting phase. The second reactor 2b and the third reactor 3 are regenerated in series by the same device for feeding with regeneration stream 11. The regeneration stream 11 is conveyed to the third reactor 3 via the feeding device 20 and the valves 6 and 22 configured for this purpose. The stream of gas resulting from the regeneration exits at the top of the third reactor 3 to the device for collecting products resulting from the third reactor 18. This regeneration gas stream is conveyed to the device for collecting the streams of gas resulting from the regeneration 12'. The valve 24 is thus configured in order to connect the device for collecting products resulting from the third reactor 18 to the device for collecting the streams of gas resulting from the regeneration 12'.

Figure 3A:
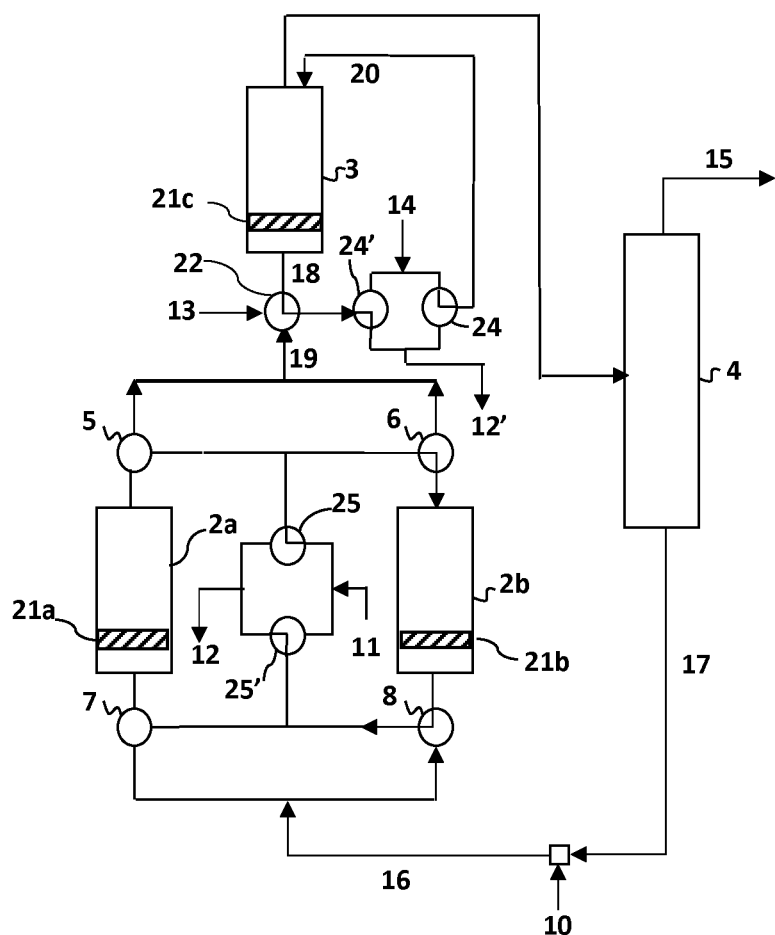
FIGS. 3a, 3b and 3c diagrammatically represent an embodiment of a plant according to the invention with three reactors comprising a device for feeding with regeneration stream at the reactor bottom and at the reactor top, in three different configurations.

FIG. 3a illustrates a specific embodiment of the present invention in which the second reactor 2b and the third reactor 3 are in the regeneration phase, the first reactor 2a being in the waiting phase. In this embodiment, the reactors can be fed with regeneration stream either at the top or at the bottom of the reactor by a device configured in order to be connected both at the top and at the bottom of the reactors. This makes it possible to regenerate alternately by the bottom of the reactor and by the top of the reactor. The second reactor 2b is fed at the top by the device for feeding with regeneration stream 11 via valves 25 and 6 configured for this purpose. The regeneration stream passes through the catalytic bed 21b in order to exit at the bottom of the second reactor 2b and to be conveyed to the device for collecting the stream of gas resulting from the regeneration 12 via the valves 8 and 25'. The third reactor 3 is fed at the top by a feeding device 20 comprising a regeneration stream resulting from the device for feeding with regeneration stream 14 via the valve 24 configured for this purpose. The regeneration stream passes through the catalytic bed 21c of the third reactor 3. The stream of gas resulting from the regeneration exits at the bottom of the third reactor 3 to the device for collecting products resulting from the third reactor 18. This regeneration gas stream is conveyed to the device for collecting the streams of gas resulting from the regeneration 12'. The valve 24' is thus configured in order to connect the device for collecting products resulting from the third reactor 18 to the device for collecting the streams of gas resulting from the regeneration 12'. No stream circulates in the first reactor 2a.

Figure 3B:
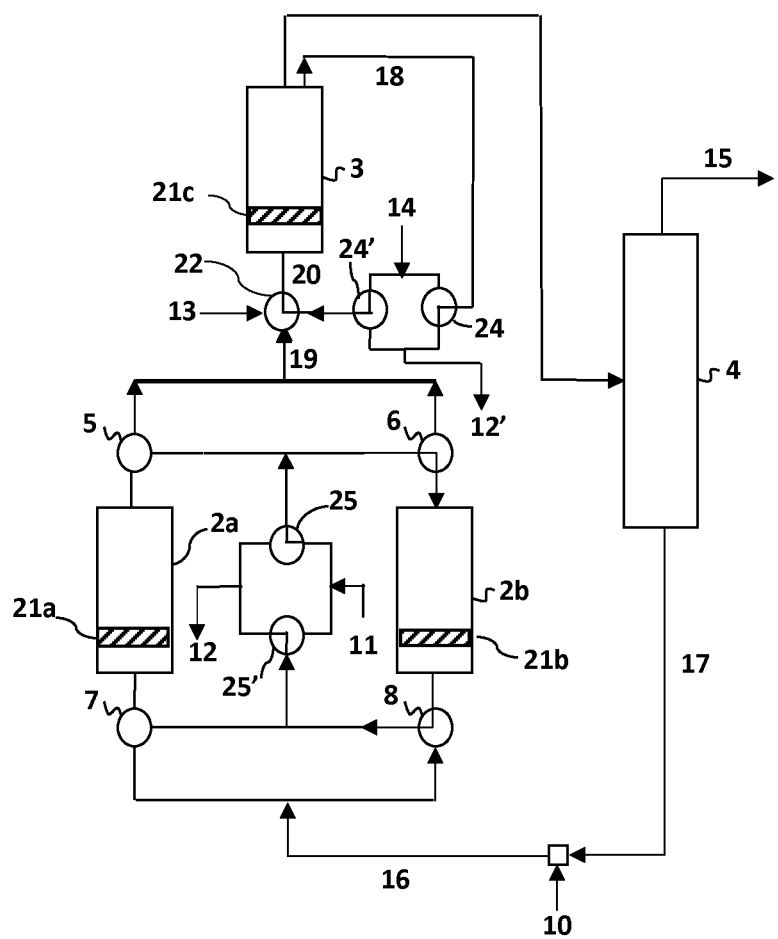

By modifying the configuration of the valves 24 and 24', the third reactor 3 can be regenerated by the bottom of the reactor. This is illustrated in FIG. 3b. The first reactor 2a and the second reactor 2b are configured in an identical way to that described in detail in connection with FIG. 3a. For its part, the third reactor 3 is fed at the bottom by a feeding device 20 comprising a regeneration stream resulting from the device for feeding with regeneration stream 14 via the valves 22 and 24' configured for this purpose. The stream of gas resulting from the regeneration is conveyed to the device for collecting products 18 at the reactor top. This regeneration gas stream is conveyed to the device for collecting the streams of gas resulting from the regeneration 12'. The valve 24 is thus configured in order to connect the device for collecting products resulting from the third reactor 18 to the device for collecting the streams of gas resulting from the regeneration 12'.

Figure 3C:
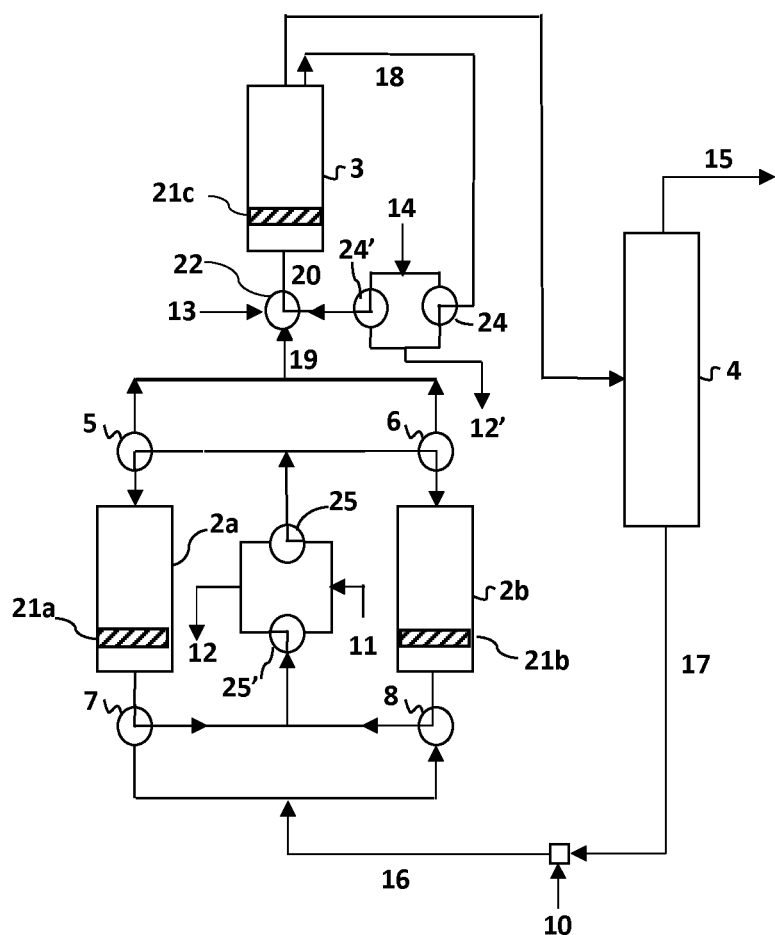

FIG. 3c illustrates a specific embodiment of the present invention in which the three reactors are in the regeneration phase. The first reactor 2a and the second reactor 2b are fed with regeneration stream by the device for feeding with regeneration stream 11. The valves 5, 6 and 25 are configured in order to make this conveyance possible. In this embodiment, the first reactor 2a and the second reactor 2b are fed at the top with the regeneration stream which respectively passes through the catalytic beds 21a and 21b. The stream of gas resulting from the regeneration is discharged from the first reactor 2a and from the second reactor 2b to the device for collecting the stream of gases resulting from the regeneration 12. The valves 7, 8 and 25' are configured in order to make this conveyance possible. The third reactor 3 is regenerated by the bottom of the reactor. The third reactor 3 is thus fed at the bottom by a feeding device 20 comprising a regeneration stream resulting from the device for feeding with regeneration stream 14 via the valves 22 and 24' configured for this purpose. The stream of gas resulting from the regeneration is conveyed to the device for collecting products 18 at the reactor top. This regeneration gas stream is conveyed to the device for collecting the streams of gas resulting from the regeneration 12'. The valve 24 is thus configured in order to connect the device for collecting products resulting from the third reactor 18 to the device for collecting the streams of gas resulting from the regeneration 12'. Of course, it is possible to have just one device for collecting the streams of gas resulting from the regeneration 12. In this case, the device for collecting products resulting from the third reactor 18 is connected to the device for collecting the streams of gas resulting from the regeneration 12, this device also being fed by the streams of gas resulting from the regeneration of the first reactor 2a and of the second reactor 2b. Alternatively, the direction of the regeneration stream can be modified in the first reactor 2a, the second reactor 2b and/or the third reactor 3. The valves 5, 6, 7, 8, 22, 24, 24', 25 and 25' are then configured in order to make it possible to convey the regeneration stream in the desired direction. This can be determined as a function of the significant or insignificant presence of coke in the reactor taken into consideration and especially of the place where the coke is formed, i.e. at the bottom or at the top of the reactor.

Figure 4A:
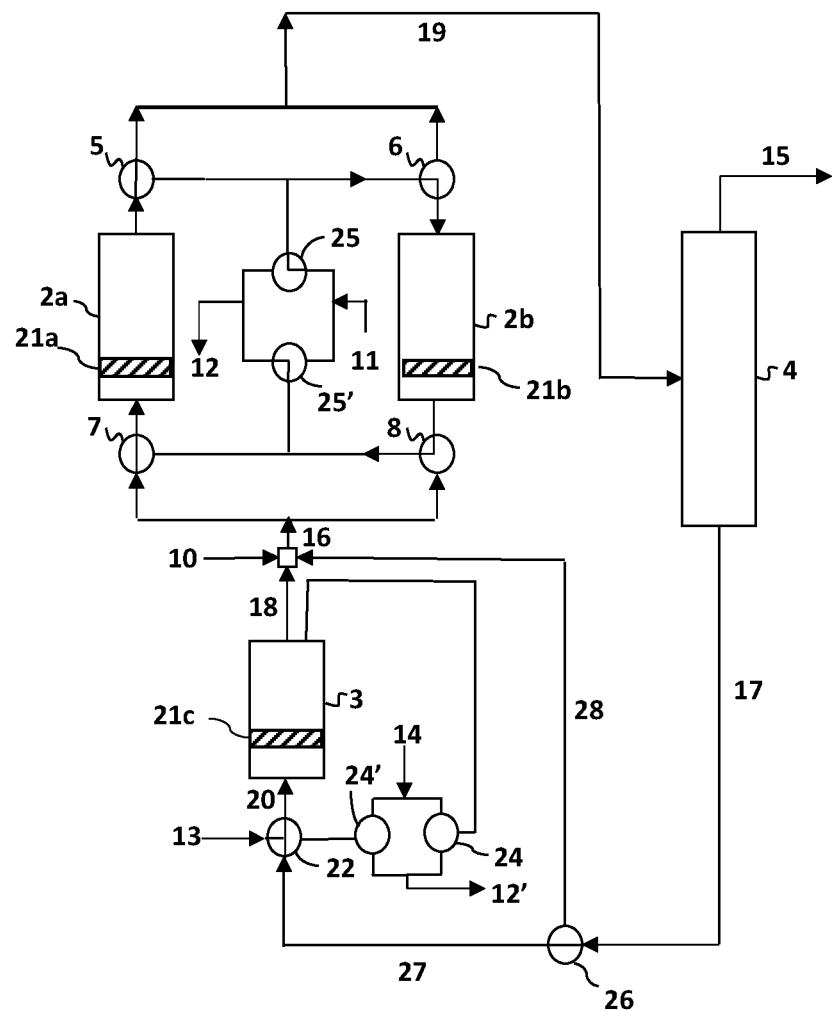
FIGS. 4a, 4b and 4c diagrammatically represent an embodiment of a plant according to the invention with three reactors comprising a device for feeding with regeneration stream at the reactor bottom and at the reactor top and a separation unit connected to the outlet of the first and of the second reactors, in three different configurations.
Figure 4B:
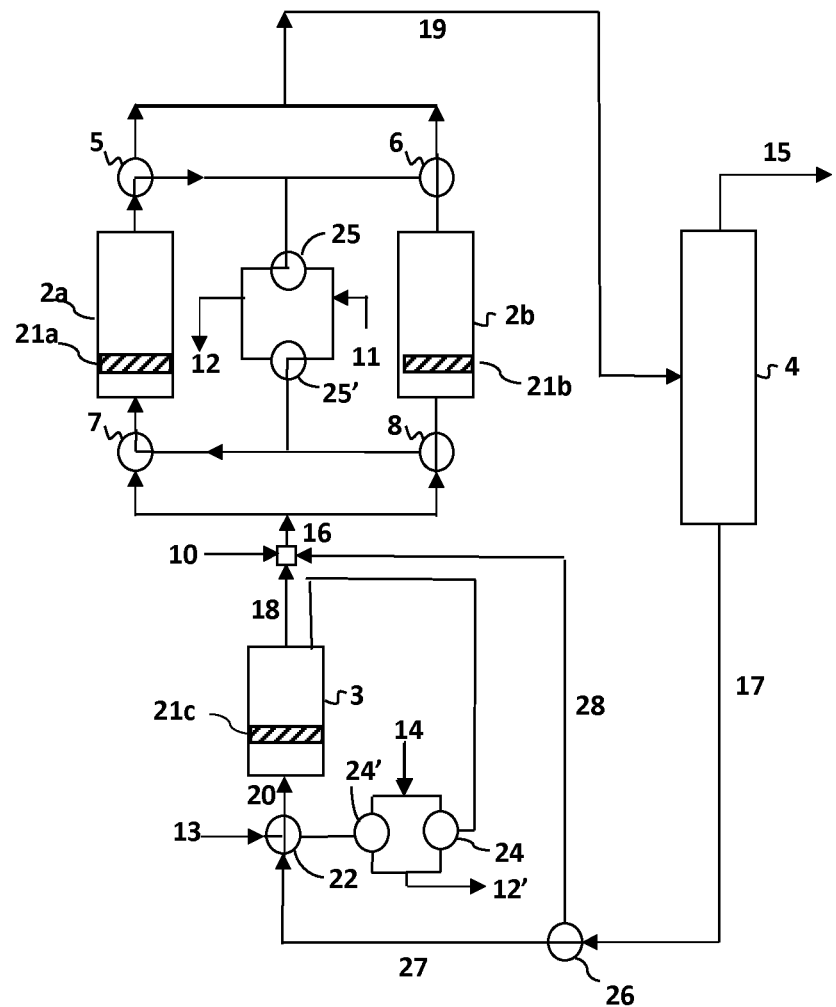
Figure 4C:
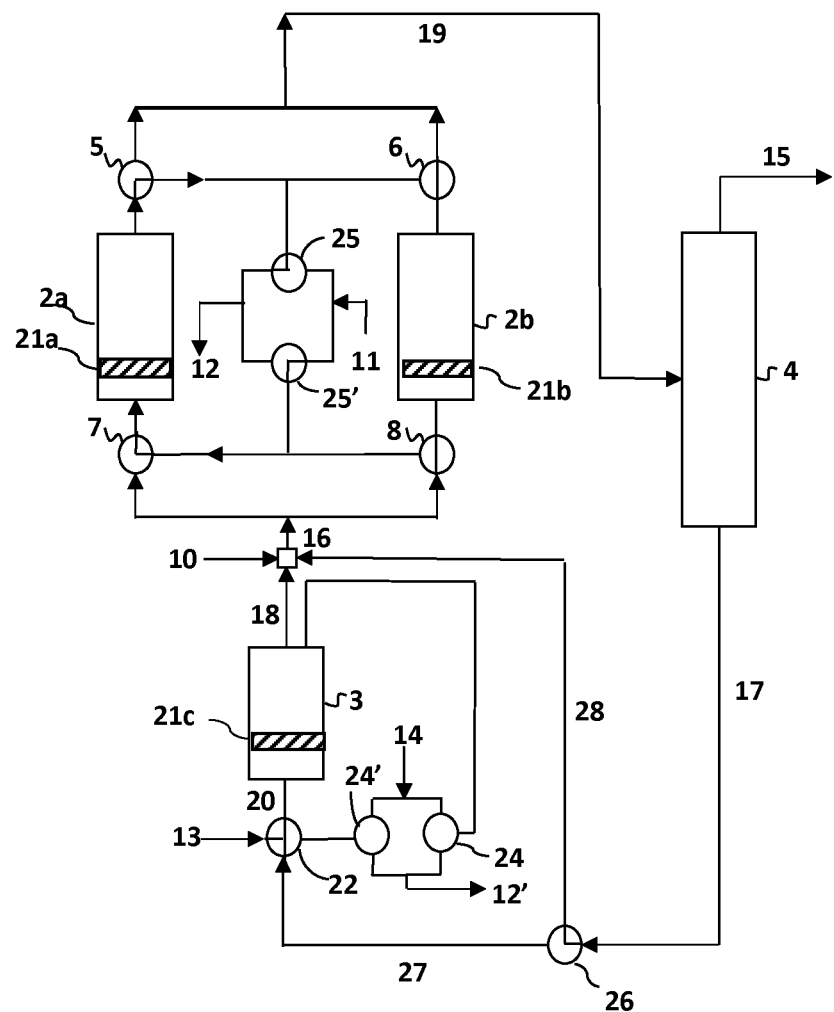

FIGS. 1a to 3c illustrate a plant in which the separation unit is positioned at the outlet of the third reactor, so as to treat the stream of products resulting from the latter. FIGS. 4a to 4c illustrate a plant in which the separation unit is positioned at the outlet of the first reactor 2a and of the second reactor 2b.

In the embodiment illustrated in FIG. 4a, the first reactor 2a is in the reaction phase, that is to say that a stage of catalytic reaction of the compound B in the presence of HF is carried out in the this reactor. The third reactor 3 is in the phase of manufacture of the compound B, i.e. reaction of the compound A with HF. The second reactor 2b is in the regeneration phase. The third reactor 3 is fed, by the device for feeding the third reader 20, with a stream of reaction mixture originating from the device for feeding with preliminary reaction mixture 13 and from the second collecting pipe 17. The preliminary reaction mixture comprises the compound A and hydrofluoric acid. The second collecting pipe 17 can comprise hydrofluoric acid and 2-chloro-3,3,3-trifluoropropene. A valve 22 makes it possible to regulate the streams resulting from the device for feeding with preliminary reaction mixture 13 and from the second collecting pipe 17. A valve 26 and an intermediate pipe 27 can be positioned between the second collecting pipe 17 and the valve 22. The valve 26 can make it possible to convey the products from the second collecting pipe 17 to the first reactor 2a and the second reactor 2b via an intermediate pipe 28 and the feeding device 16 without passing through the third reactor 3. The preliminary reaction mixture resulting from the device for feeding the third reader 20 comes into contact with the preliminary catalyst present in the catalytic bed 21c. The products of the reaction are conveyed, via the device for collecting stream of products from the third reactor 18, to the device for feeding 16 the first reactor 2a or the second reactor 2b. The device for collecting stream of products from the third reactor 18 comprises in particular the compound B. The products resulting from the third reactor can be mixed with hydrofluoric acid resulting from the device for feeding with hydrofluoric acid 10 and/or with the products conveyed by the second collecting pipe 17 via the intermediate pipe 28, in order to form the reaction mixture used in the reaction stage carried out in the first reactor 2a. The reaction mixture is brought into contact, in the first reactor 2a, with the catalyst present in the catalytic bed 21a. The products resulting from this reaction stage in the first reactor 2a are conveyed to the intermediate collecting device 19 and to the separation unit 4 described in connection with FIG. 1a. The second reactor 2b is in the regeneration phase. The regeneration stream is conveyed, by the device for feeding with regeneration stream 11, to the top of the second reactor 2b. The stream of gas resulting from the regeneration of the catalyst present in the catalytic bed 21b is conveyed to the device for collecting the streams of gas resulting from the regeneration 12. The direction of the reaction stream and of the regeneration stream is reversed in this embodiment.

FIG. 4b illustrates an embodiment in which the first reactor 2a is in the regeneration phase and the second reactor 2b carries out a stage of reaction of the compound B with HF. The third reactor 3 carries out a stage of reaction of a compound A with HF, as described in FIG. 4a. In this embodiment, the streams in the first reactor 2a and the second reactor 2b are in the same direction.

FIG. 4c illustrates an embodiment as described in connection with FIG. 4a, except that the products from the second collecting pipe 17 are conveyed to the first reactor 2a via an intermediate pipe 28 and the feeding device 16 without passing through the third reactor 3.

The invention makes it possible to optimize the manufacture of tetrafluoropropene (HFO-1234yf or HFO-1234ze) by alternating the cycles of regeneration and of manufacture of the tetrafluoropropene with three reactors. The invention also makes it possible to improve the regeneration stage by making it possible to carry out the latter alternately by the bottom or the top of the reactor in order to prevent the accumulation of coke in the reactor.

The invention claimed is:

1. A process for the manufacture of tetrafluoropropene employing three reactors and comprising the stages of:
carrying out, in the first and the second reactor, at least one stage of reaction in the gas phase of a compound B in the presence of hydrofluoric acid and of a catalyst, in order to form the tetrafluoropropene; alternately with a stage of regeneration of the catalyst by bringing the latter into contact with a regeneration stream comprising an oxidizing agent,
carrying out, in the third reactor, a preliminary stage of manufacture of the compound B using a preliminary catalyst, alternately with a stage of regeneration of the preliminary catalyst with a regeneration stream comprising an oxidizing agent, wherein:

when the stage of regeneration of the preliminary catalyst in the third reactor is carried out, the first reactor and the second reactor are, independently of one another, either in a phase of regeneration of the catalyst or in a waiting phase.

2. The process as claimed in claim 1, further comprising:

collecting a stream of products on conclusion of the preliminary stage of manufacture of the compound B;

using said stream of products in order to carry out the stage of reaction of the compound B in the presence of hydrofluoric acid; and separating the stream of products resulting from the stage of reaction of the compound B in the presence of hydrofluoric acid into a first stream comprising hydrochloric acid and tetrafluoropropene and a second stream comprising hydrofluoric acid and the compound B;

optionally, collecting said second stream comprising hydrofluoric acid and the compound B, and the recycling said second stream in the stage of reaction of the compound B with hydrofluoric acid or of the preliminary stage of manufacture of the compound B.

3. The process as claimed in claim 1, wherein the stage of regeneration of the preliminary catalyst in the third reactor is carried out simultaneously with the stage of regeneration of the catalyst in the first reactor or the second reactor or both.

4. The process as claimed in claim 1, wherein, in the first reactor and the second reactor, the stage of reaction of a compound B in the presence of hydrofluoric acid is carried out alternately with the regeneration stage.

5. The process as claimed in claim 1, wherein the reactors are made of steel and have an interior surface covered with an alloy comprising more than 30% by weight of nickel or with a fluoropolymer-type coating.

6. The process as claimed in claim 1, wherein the tetrafluoropropene comprises 2,3,3,3-tetrafluoropropene or 1,3,3,3-tetrafluoropropene.

7. The process as claimed in claim 1, wherein the preliminary stage of manufacture of compound B is a preliminary stage of reaction in the gas phase of a compound A in the presence of hydrofluoric acid and of a preliminary catalyst, said compound A being different from said compound B, wherein the compound A is selected from the group consisting of tetrachloropropenes, chlorotrifluoropropenes, pentachloropropanes, dichlorotrifluoropropanes, trichlorodifluoropropanes, tetrachlorofluoropropanes, dichlorodifluoropropenes, trichlorofluoropropenes and the mixtures of these; and the compound B is selected from the group consisting of chlorotrifluoropropenes, pentafluoropropanes, dichlorotrifluoropropanes, trichlorodifluoropropanes, tetrachlorofluoropropanes, dichlorodifluoropropenes, trichlorofluoropropenes and the mixtures of these.

8. The process as claimed in claim 1, wherein the regeneration stream is in the same direction or in the reverse direction, with respect to the direction of introduction into the first reactor or the second reactor of a reaction stream comprising the compound B and hydrofluoric acid.

9. The process as claimed in claim 1, wherein the direction of the regeneration stream is alternated at each regeneration stage.

* * * * *